United States Patent [19]

Lonardo

[11] Patent Number: 4,926,884
[45] Date of Patent: May 22, 1990

[54] METHOD AND MEANS FOR PREVENTING SKIN ABRASIONS FOR PATIENTS HAVING LEGS SUBSTANTIALLY LOCKED IN JUXTAPOSITION

[75] Inventor: Robert Lonardo, Treasure Island, Fla.

[73] Assignee: L'Nard Associates, Inc., St. Petersburg, Fla.

[21] Appl. No.: 255,013

[22] Filed: Oct. 7, 1988

Related U.S. Application Data

[63] Continuation-in-part of Ser. No. 107,980, Oct. 14, 1987, abandoned.

[51] Int. Cl.⁵ ............................................. A61B 19/00
[52] U.S. Cl. ..................................... 128/892; 128/165; 2/22
[58] Field of Search ....................... 128/165, 892; 2/22

[56] References Cited

U.S. PATENT DOCUMENTS

| | | | |
|---|---|---|---|
| 1,801,437 | 4/1931 | Lown et al. | 2/22 |
| 2,532,955 | 12/1950 | Shook | 128/165 |
| 2,606,554 | 8/1952 | Simon | 128/165 |
| 3,189,919 | 6/1965 | Chase | 2/22 |
| 3,975,015 | 8/1976 | Owens et al. | 128/165 |
| 4,090,508 | 5/1978 | Gaylord, Jr. | 128/165 |
| 4,177,806 | 12/1979 | Griffin | 2/22 |
| 4,433,682 | 2/1984 | Badra | 128/892 |
| 4,736,477 | 4/1988 | Moore | 128/165 |

*Primary Examiner*—Robert A. Hafer
*Assistant Examiner*—Charles H. Sam

*Attorney, Agent, or Firm*—Zarley McKee, Thomte, Voorhees & Sease

[57] ABSTRACT

The method of this invention pertains to preventing skin abrasions and the like in patients whose legs are substantially locked together in juxtaposition. The method comprises the taking of an elongated flexible planar pad with a length extending from above the patient's knees to the bottom of the patient's foot. The width of the pad is approximately one-half of the girth of one of the patient's legs. The pad is placed between the patient's legs so that the opposite sides of the pad cover the inner surface of at least one leg from a point above the knee to a point substantially to the bottom of the foot of one leg. The pad is affixed to one leg of the patient at points above the knee and above the ankle of one leg to hold the pad against any substantial movement with respect to the one leg. The apparatus of this invention comprises a pad for the foregoing method. The pad is a flexible planar pad having a top, a bottom, side edges, and opposite leg engaging surfaces. The leg engaging surfaces comprise a soft resilient material so that the skin and flesh of the inner portion of a patient's legs will be protected from abrasive action. A first strap means is secured to the pad adjacent its upper end for securing the pad to a patient's leg just above the knee. A second strap means is secured to the pad adjacent the bottom thereof for securing the pad to the patient's leg just above the ankle. Tubular tape elements are sewn adjacent slot openings that accommodate the strap means. Rigid stays extend through the tape elements.

10 Claims, 3 Drawing Sheets

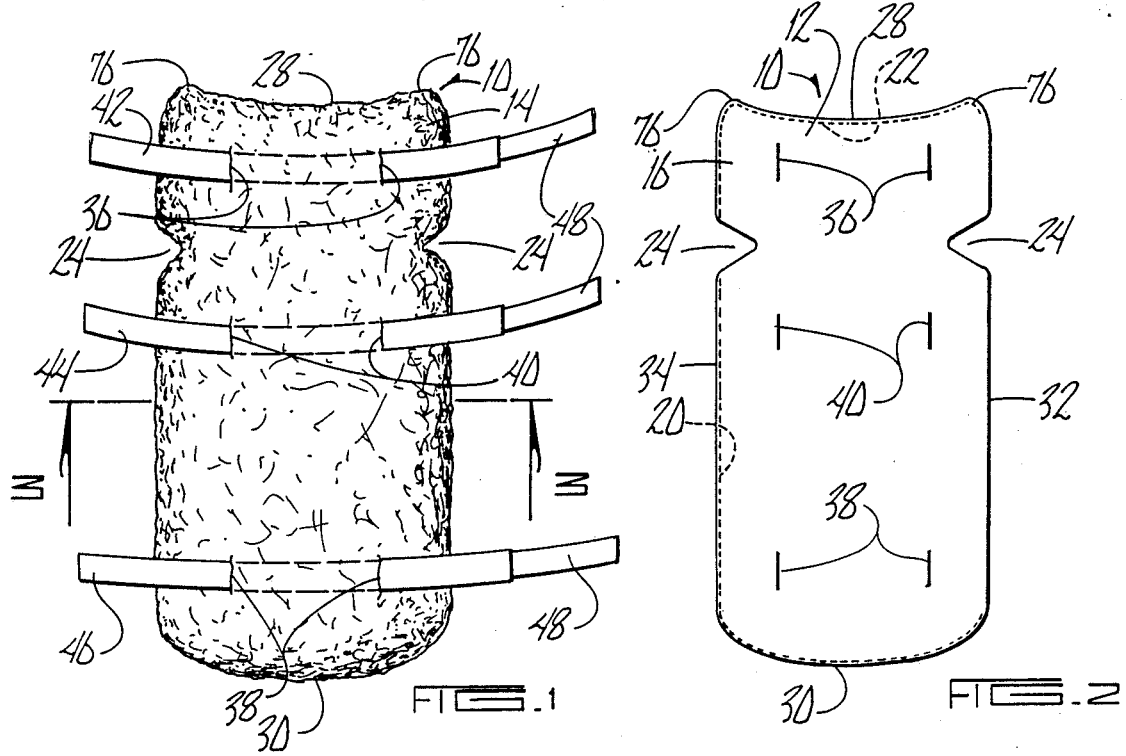
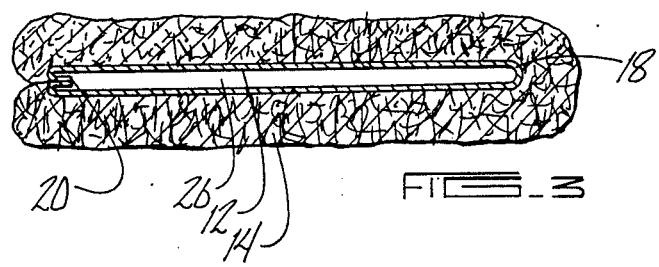
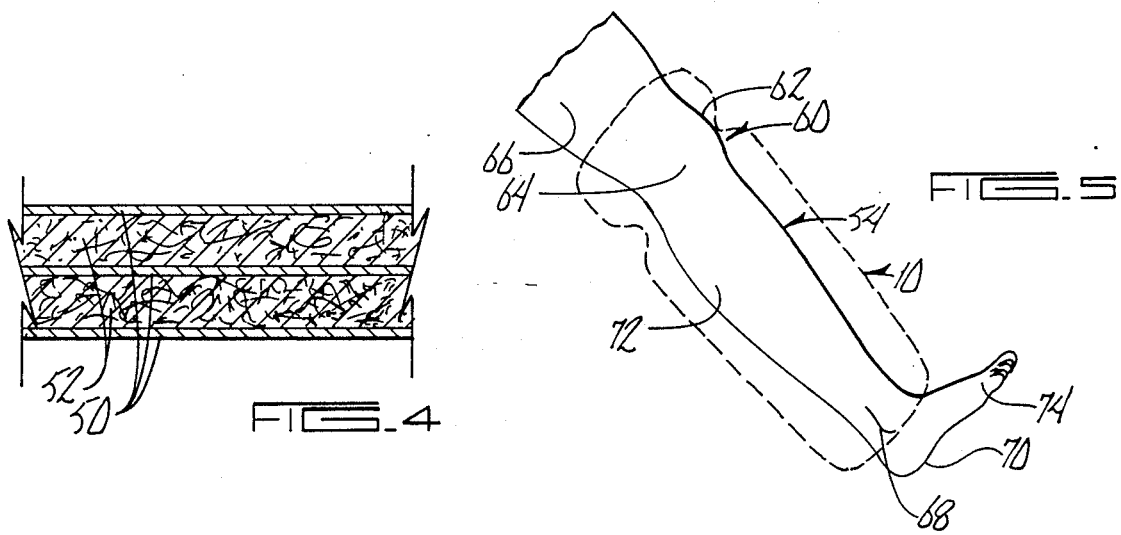

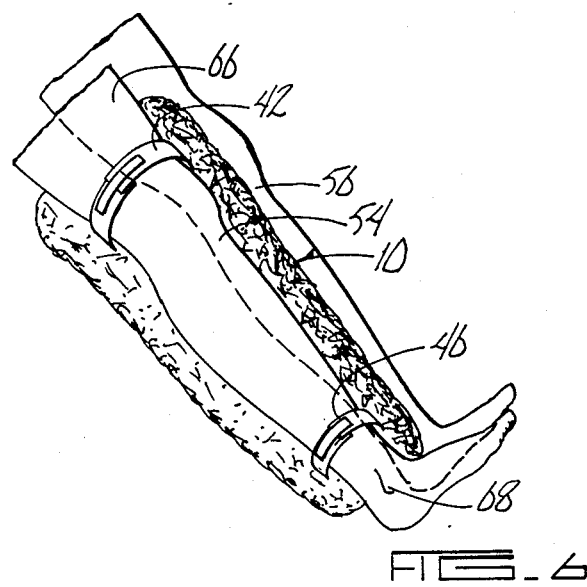
FIG_6
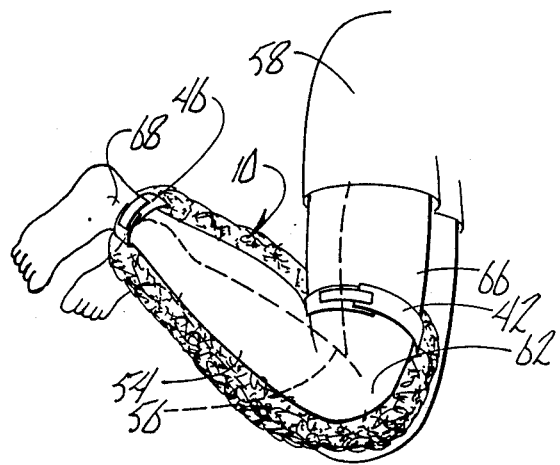
FIG_7

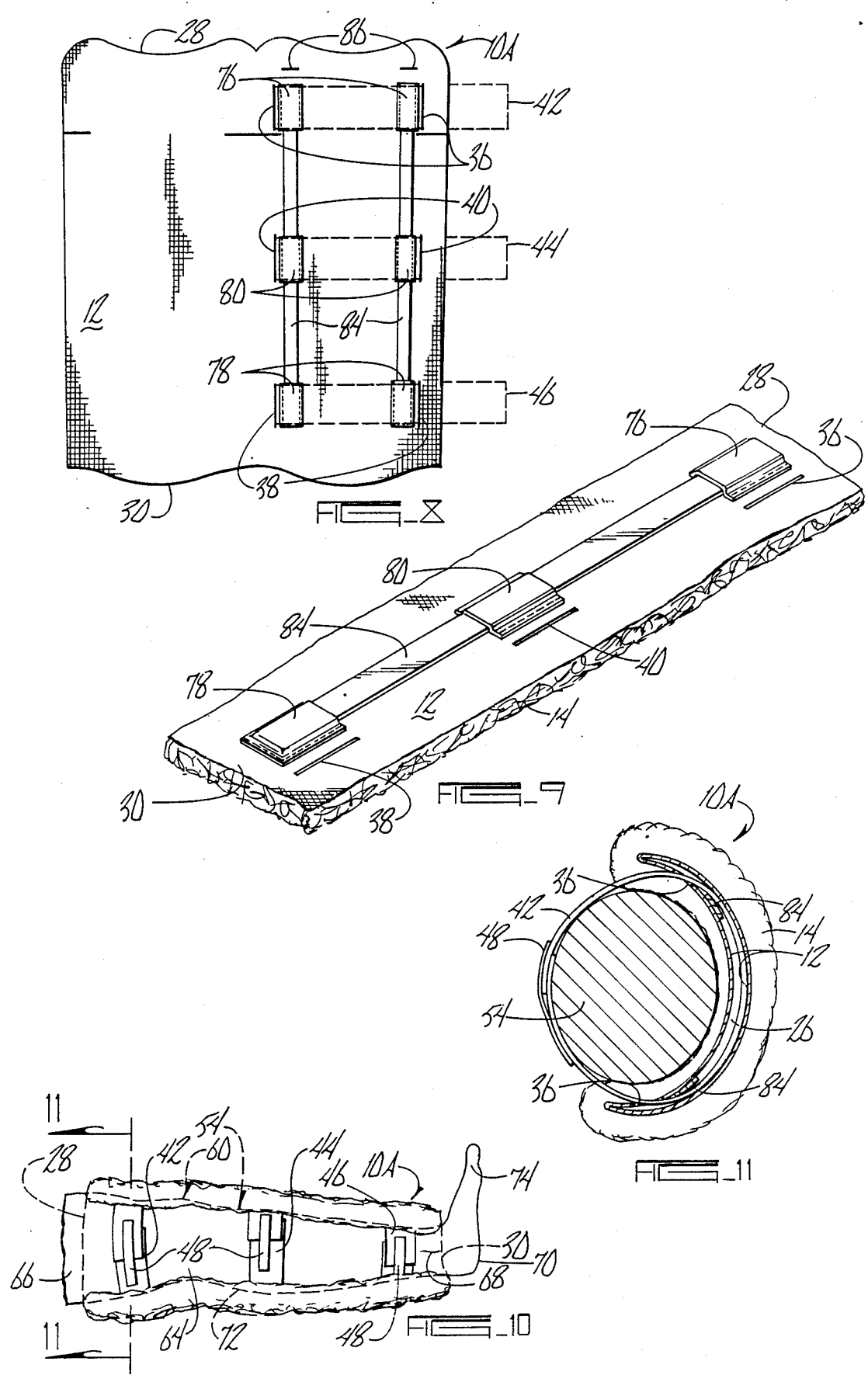

METHOD AND MEANS FOR PREVENTING SKIN ABRASIONS FOR PATIENTS HAVING LEGS SUBSTANTIALLY LOCKED IN JUXTAPOSITION

This application is a continuation-in-part of co-pending application Ser. No. 107,980, filed Oct. 14, 1987 now abandoned.

BACKGROUND OF THE INVENTION

Many bedridden patients, usually paralysis victims, have their legs substantially locked together in close juxtaposition. This condition is known as valgus wherein the muscles of the hip contract so that the legs cannot be spread. Such patients normally lay on their sides in a fetal position. Skin abrasions, sores and ulcers often are created at the knees, ankles and feet where the non-muscular portions of the legs tend to more forcibly engage. Slight movement of either leg aggravates this situation.

Pillows of the like are often forcibly inserted between such a patient's legs. However, pillows are often of improper thickness, and do not stay in place.

Therefore, a principal object of this invention is to provide a method and means for preventing skin abrasions for patients having legs substantially locked in juxtaposition which will prevent abrasion between the patient's legs as they bear against each other.

A further object of the invention is to provide a method and means for preventing skin abrasions for patients having legs substantially locked in juxtaposition which will prevent abrasion between the patient's legs as they bear against each other, and which will maintain this protection regardless of patient movement.

A still further object of this invention is to provide a means for preventing skin abrasions for patients having legs substantially locked in juxtaposition which is easily attached to the patient.

A still further object of this invention is to provide a means for preventing skin abrasions for patientshaving legs substantially locked in juxtaposition which is comfortable to the patient.

A still further object of this invention is to provide a means for preventing skin abrasions for patients having legs substantially locked in juxtaposition which can be easily removed, cleaned and reused.

A still further object of this invention is to provide a means for preventing skin abrasions for patients having legs substantially locked in juxtaposition which will not interfere with the blood circulation in the patient's legs.

A still further object of this invention is to provide a means for preventing skin abrasions for patients having legs substantially locked in juxtaposition which will only partially encompass one of the patient's legs to keep the leg from becoming unduly warm.

A still further object of this invention is to provide a means for preventing skin abrasions for patients having legs substantially locked in juxtaposition which can be used on either leg of the patient.

A still further object of this invention is to provide a flexible pad means for patients having legs in substantially overlapped position wherein therein cause the pad to be wrapped around a portion of the patient's leg to conform the pad to the shape of the patient's leg.

A still further object of this invention is to provide a flexible pad means for patients having legs in substantially overlapped position wherein strap means extend through slots in the pad to cause the pad to be wrapped around a portion of the patient's leg to conform the pad to the shape of the patient's leg with tape means being secured to the pad adjacent the slots to help uniformly distribute the pulling load of the straps.

A still further object of this invention is to provide a flexible pad means for patients having legs in substantially overlapped position wherein strap means extend through slots in the pad to cause the pad to be wrapped around a portion of the patient's leg to conform the pad to the shape of the patient's leg with tape means being secured to the pad adjacent the slots to help uniformly distribute the pulling load of the straps with elongated stays being positioned by tubular openings in the tape means.

These and other objects will be apparent to those skilled in the art.

SUMMARY OF THE INVENTION

The method of this invention pertains to preventing skin abrasions and the like in patients whose legs are substantially locked together in juxtaposition. The method comprises the taking of an elongated flexible planar bed with a length extending from above the patient's knee to the bottom of the patient's foot. The width of the pad is approximately one-half of the girth of one of the patient's legs. The pad is placed between the patient's legs so that the opposite sides of the pad cover the inner surface of at least one leg from a point above the knee to a point substantially to the bottom of the foot of one leg. The pad is affixed to one leg of the patient at points above the knee and above the ankle of one leg to hold the pad against any substantial movement with respect to the one leg.

The apparatus of this invention comprises a pad for the foregoing method. The pad is a flexible planar pad having a top, a bottom, side edges, and opposite leg engaging surfaces. The leg engaging surfaces comprise a soft resilient material so that the skin and flesh of the inner portion of a patient's legs will be protected from abrasive action. A first strap means is secured to the pad adjacent its upper end for securing the pad to a patient's leg just above the knee. A second strap means is secured to the pad adjacent the bottom thereof for securing the pad to the patient's leg just above the ankle. A third strap means can be used alternately, and it is secured to the pad just below the knee portion to again secure the pad to the leg of the patient just below the knee.

The pad is formed by a layer of canvas material to which is affixed the soft resilient material which forms the padding thereof. The canvas material is folded along a central seam, and the outer periphery of the overlapped portions of the pad are then sewn together.

Opposite notch elements are cut into the pad at the side edges towards the upper portion thereof. These notched edges are not sewn and form an access to the interior compartment of the pad.

The strap means are threaded through opposite pairs of vertical slots in one surface of the pad. Tape means are sewn to the pad adjacent the vertical slots. Elongated stiffening stays extend through longitudinally aligned tubular openings in the tape means.

The upper portion of the pad is formed in a downwardly extending concave shape, and the bottom of the pad is formed in a downwardly extending convex shape.

BRIEF DESCRIPTION OF THE DRAWINGS

FIG. 1 is a plan view of the pad of this invention;

FIG. 2 is a plan view of the pad of this invention during an initial stage of fabrication with the strap elements omitted therefrom;

FIG. 3 is an enlarged scale sectional view taken on line 3—3 of FIG. 1;

FIG. 4 is a partial sectional view at an enlarged scale taken through one of the strap elements;

FIG. 5 is an elevational view of one leg of a patient;

FIG. 6 is a partial perspective view of the opposite side of the leg shown in FIG. 5 with the pad attached thereto;

FIG. 7 is a perspective view of the pad of this invention affixed to the leg of a patient in a position different that that of FIG. 6;

FIG. 8 is a plan view of the pad of an alternate form of the invention before final assembly;

FIG. 9 is an enlarged partial perspective view of the device of FIG. 8 showing the stiffening stays in place;

FIG. 10 is an elevational view of a patient wearing the pad of FIGS. 8 and 9; and FIG. 11 is an enlarged scale sectional view taken on line 11—11 of FIG. 10.

DETAILED DESCRIPTION OF THE PREFERRED EMBODIMENT

The numeral 10 designates the pad of this invention which is comprised of canvas layer 12, with a soft resilient padding material 14 secured to one surface thereof. The material 14 is a washable polyester fiber having the texture of wool fleece and is available under the trademark "Kodel." The pad 10 is symmetrically cut about a center fold 16 and thereupon folded on both center folds 16 and fold 18 into the configuration shown in FIG. 2. At that stage of the fabrication, the canvas layer 12 is on the outside. The lower portion of the pad is then secured together by sewn seam 20. The pad is then turned inside out so that the material 14 appears on the outside thereof, and seam 22 is then put in place to substantially enclose the interior of the pad.

V-shaped notches 24 are cut in opposite sides of the pad near the top thereof. The notches are not sewn closed and serve as access to the interior compartment 26 of the pad. Access to the interior compartment 26 is desirable as will be described hereafter.

The pad 10 includes a top 28 which has a concave shape that extends downwardly, and a bottom 30 which has a convex shape which also extends downwardly. The numerals 32 and 34 designate the side edges of the pad.

A first pair of vertical cuts or slots 36 are located in the upper portion of the pad. A second pair of spaced vertical slots 38 are located towards the bottom portion of the pad; and a third pair of spaced vertical slots 40 are located immediately below the notches 24. A first strap 42 is threaded through slots 36; a second strap 44 is threaded through slots 38; and a third strap 46 can be threaded through slots 40 if it is desired to have a securing means at that point on the leg. The firs strap 42 is adapted to secure the pad to the leg immediately above the knee; the second strap 44 is adapted to secure the pad to the leg immediately above the ankle; and the third strap 46, if needed, is adapted to secure the pad to the leg immediately below the knee. It should be noted that the horizontal space between slots 36 is slightly greater than the horizontal space between the lower slots 38 (six inches versus four inches). A conventional Velcro strap 48 is secured to one end of each of the straps and is adapted to fix the free ends of the straps together in conventional fashion.

Each of the straps is comprised of three felt layers 50 (see FIG. 4) which have foam layers 52 interposed therebetween. These straps are soft and are slightly resilient and are intended to be very comfortable to the leg of the patient.

The dimensions for a typical pad 10 adapted for use on an adult are as follows: The vertical height of the pad is approximately 23 inches. The notches 24 are approximately 1½ inches in vertical height and extend no more than 2½ inches into the body of the pad from the side edges thereof. The vertical slots described above are approximately two inches in length. The width of the pad at the top is approximately 12 inches, and the width of the lower end is approximately eight inches. The slots 36 are approximately two inches from the top 28, and the slots 38 are approximately two inches from the bottom 30. The first strap 42 is approximately 18½ inches in length and the lower strap 44 is approximately 15 inches in length. The third strap 46, if used should be approximately 15 to 18½ inches in length, and preferably closer to 18½ inches in length. The notches 24 are approximately five inches from the top 28 of the pad. The thickness of the material 14 is approximately three inches but obviously can be compressed to ½ inch to ¾ inches.

FIGS. 6 and 7 show a patient's legs 54 and 56. With reference to FIG. 5, the numeral 58 designates a patient's thigh; the numeral 60 designates the knee area; the numeral 62 designates the kneecap; the numeral 64 designates the knee joint. The numeral 66 shows the area of the thigh which includes the quadracep muscle group. The numeral 68 designates the ankle, with the numerals 70, 72 and 74 designating the patient's heel, calf and foot.

With reference to FIGS. 8-11, the alternative pad 10A is essentially identical to pad 10 except as pointed out hereafter. Tubular tape elements 76, 78 and 80 comprised of canvas or the like are sewn to the interior of pad 10A adjacent slots 36, 38 and 40, respectively. The sides of tape elements are sewn to the pad with the ends remaining open except for the lower end 82 of tape element 78 which is sewn closed. Elongated rigid stays 84 of metal or the like are inserted into the aligned tape elements to make the pad 10A rigid when the stays are in place. Access openings 86 are provided in pad 10A to permit the stays to be inserted or removed even after the pad 10A is assembled.

The normal operation of the device of this invention, as shown in FIGS. 1-7, is as follows: With at least the straps 42 and 44 attached to the pad, the pad is inserted between the legs 54 and 56 of the patient. The ends of the straps 42 and 44 are secured together just above the knee and just above the ankle as described above by utilizing the Velcro fastener 48. Since the spacing between slots 36 and slots 38 are approximately the "diameter" of the patient's leg at those respective points, the straps pull the pad into close engagement with the leg but do not serve to squeeze the leg so as to impede blood circulation in the leg. With the lower strap 44 being between the ankle and the calf of the leg, and the upper strap 42 being between the knee and the major diameter of the thigh, the pad 10 is held substantially immobile on the leg. However, as slight bending of the knee takes place, the notches 24 permit the lower portion of the pad below the notches to flex freely even though the portion of the pad above the notches and above the knee remain substantially stationary. Preferably, the notches 24 are positioned slightly below the kneecap 62. The corners 76 of the pad serve to maintain padded material between the legs of the patient even though the leg may flex slightly to displace the pad above the knee.

It is important that the lower end or bottom 30 of the pad extend substantially to the medial distal heel to cover all pressure points that might exist between the patient's two legs.

The pad 10 serves to equalize the pressure exerted by the weight or pressure of one leg on the other and relieves the high pressure points between the heels, ankles, and knees of the patient.

The straps of the pad can be washed by removal thereof, and they can be replaced when necessary. This is accomplished by reaching the hand inside the interior of the pad and manipulating the strap out of the vertical slots in which the strap is mounted.

Similarly, the pad can be removed from the patient, laundered, and reused.

The pad 10A of FIGS. 8-11 is useful for patients who require a splint-type pad of substantial rigid character. The stays 84 described heretofore provide the necessary rigid quality to the pad 10A.

The tape elements 76, 78 and 80 not only retain the stays 84, but they reinforce the edges of slots 36, 38 and 40 so to distribute the pulling action of the securing straps over a greater area. Without the tape elements being present, the pad sometimes has a tendency to "gather" or fold adjacent the slots when the straps are tightened to wrap the pad around the leg of the patient. FIG. 11 shows how the straps wrap the pad around the leg of the patient to cause it to conform to the shape of the leg. The stays are not in contact with the leg.

Thus, from the foregoing, it is seen that this device will accomplish at least all of its stated objectives.

I claim:

1. A pad for preventing skin abrasions and the like for use between the legs of patients whose legs are substantially positioned in overlapping condition, comprising, a flexible planar pad having an interior compartment and having a top, a bottom, side edges, and opposite leg engaging surfaces, including surfaces to permit simultaneous engagement with opposed heels, ankles, or knees of said patient, a first pair of spaced substantially vertical slots adjacent the top of one of said leg engaging surfaces, a second pair of spaced substantially vertical slots adjacent the bottom of said one of said leg engaging surfaces, said leg engaging surfaces comprising a soft resilient material so that the skin and flesh of the inner portion of a patient's legs will be protected from abrasive friction when said pad is placed between the legs of a patient whose legs are subtantially locked together in overlapping condition, whereby the pressure exerted by the weight of one leg on the other can be equalized, and the pressure points between heels, ankles and knees of the patient can be relieved when said heels, ankles or knees are in overlapping condition, first strap means, having a center portion and opposite end portions, threaded through said first pair of vertical slots so that the center portion thereof dwells within said interior compartment and said end portions thereof extend over said side edges to be joined on the side of said patient's leg opposite to said center portion thereof, for securing said pad to a patient's leg above the knee, and a second strap means, having a center portion and opposite end portions, threaded through said first pair of vertical slots so that the center portion thereof dwells within said interior compartment and said end portions thereof extend over said side edges to be joined on the side of said patient's leg opposite to said center portion thereof, for securing said pad to a patient's leg above the ankle, said first and second strap means being capable of pulling said pad into engagement with a patient's leg as the end portions thereof extend over said side edges and are joined, respectively, on the side of a patient's leg opposite to said pad so that said pad will conform to the shape of the patient's leg.

2. The device of claim 1 wherein said first strap means is adapted to extend around the leg of the patient above the kneecap and below the quadricep muscle.

3. The device of claim 2 wherein said second strap means is adapted to extend around the leg of the patient above the ankle and below the calf muscles thereof.

4. The device of claim 1 wherein a pair of spaced rigid stays are removably secured within said interior compartment to provide rigidity to said pad when affixed to a patient's leg.

5. The device of claim 1 wherein a third pair of spaced substantially vertical slots are positioned between said first and second pair of slots, and a third strap means is threaded through said third pair of straps and being adapted to secure said pad to a patient's leg below the knee.

6. The device of claim 1 wherein the vertical length of said pad normally extends from above the patient's knees to the bottom of the patient's feet, and the width of said pad is approximately one-half the girth of one of the patient's legs.

7. The device of claim 1 wherein tape means are secured to said pad adjacent said first and second pair of slots to reinforce said pad and to enhance the ability of said straps to conform said pad to the shape of a patient's leg.

8. The device of claim 7 wherein said tape means has a tubular shape, and a pair of rigid stays extend through said tape means adjacent one each said first and second pairs of slots, respectively, to provide rigidity to said pad when affixed to a patient's leg.

9. The device of claim 8 wherein said stays are located within said interior compartment so as to be free from direct engagement with a patient's leg.

10. The device of claim 9 wherein access openings are located in said pad to permit insertion and removal of said stays with respect to said interior compartment.

* * * * *